US006822432B2

(12) United States Patent
Hilleary

(10) Patent No.: US 6,822,432 B2
(45) Date of Patent: Nov. 23, 2004

(54) METHODS AND SYSTEMS FOR AUTOMATED PIPELINE TESTING

(75) Inventor: Thomas N. Hilleary, Chesterfield, MO (US)

(73) Assignee: Network Technologies Group, LLC, Lenexa, KS (US)

( * ) Notice: Subject to any disclaimer, the term of this patent is extended or adjusted under 35 U.S.C. 154(b) by 0 days.

(21) Appl. No.: 10/096,200

(22) Filed: Mar. 12, 2002

(65) Prior Publication Data

US 2002/0196008 A1 Dec. 26, 2002

Related U.S. Application Data

(60) Provisional application No. 60/300,348, filed on Jun. 22, 2001.

(51) Int. Cl.$^7$ .................. G01R 31/02; G08B 26/00; G01N 17/04; H04B 17/00

(52) U.S. Cl. .................. 324/72; 324/72.5; 324/71.2; 340/505; 340/645; 205/775.5; 455/67.11

(58) Field of Search .................. 324/72, 72.5, 71.2, 324/700, 330, 347, 348; 205/775.5, 776.2; 204/196.03, 196.06; 73/865.8, 786, 40.5 R; 340/500, 505, 517, 645, 865.3; 455/423, 450, 455, 515, 516, 67.11

(56) References Cited

U.S. PATENT DOCUMENTS

2002/0155832 A1 10/2002 Stucky et al.
2002/0158778 A1 10/2002 Lash et al.
2002/0171438 A1 11/2002 Dudley

*Primary Examiner*—Anjan K. Deb
(74) *Attorney, Agent, or Firm*—Armstrong Teasdale LLP

(57) ABSTRACT

A system and method for testing a cathodic protection system includes a cathodic protection rectifier configured to apply a voltage across a pipeline and a reference point. The method includes measuring a magnitude of an output voltage of the cathodic protection rectifier, transmitting to a site remote from the rectifier, the measured output voltage magnitude using a cellular control channel, receiving the transmitted measurement at the remote site, and using the transmitted measurement to determine whether the cathodic protection system is operational.

44 Claims, 12 Drawing Sheets

Major Components of the Cellular Telephone Network

Wireless Data Technology Options

Roaming Registration Packet

METHODS AND SYSTEMS FOR AUTOMATED PIPELINE TESTING

CROSS REFERENCE TO RELATED APPLICATIONS

This application claims the benefit of U.S. Provisional Application No. 60/300,348, filed Jun. 22, 2001, which is hereby incorporated by reference in its entirety.

BACKGROUND OF THE INVENTION

This invention relates generally to underground pipelines, and more specifically to maintenance and testing of underground pipelines.

Pipelines and other metallic structures are inherently inclined to corrode. The corrosion process involves the removal of electrons or oxidation of the metal, and consumption of those electrons by some other reduction reaction, such as oxygen or water reduction. Corrosion is encouraged by the presence of moist soil in contact with a metal pipeline.

The electrochemical nature of the corrosion process provides opportunities to detect and mitigate corrosion of underground structures. Typical mitigation methods include applications of coatings to the structures and neutralizing the voltages and currents associated with the corrosion process through application of external voltages and currents.

Corrosion mitigation processes can be monitored to determine the extent of corrosion activity and to verify the effectiveness of electrical corrosion prevention systems. One known electrical corrosion prevention system for application of external voltages and currents to an underground structure, such as a pipeline, is referred to as a cathodic protection system. As part of the maintenance process, corrosion mitigation processes are monitored to determine the extent of corrosion activity. As a result, effectiveness of the cathodic protection system is also monitored.

The U.S. pipeline industry has standardized methods for assessing the performance of a cathodic protection rectifier system. One method used to detect corrosion activity and to assure the proper performance of the cathodic protection systems includes reading and verifying the output voltage of cathodic protection rectifiers, and reading and verifying the impressed current on the pipeline by measuring the voltage drop across a shunt resistor connected in series with the output of a cathodic protection rectifier. U.S. governmental regulations currently in place require measurement of rectifier voltage outputs at least once every two months.

Another conventional pipeline test, sometimes called an "on" potential measurement, includes reading the pipe-to-soil voltage at test points along the pipeline with cathodic protection rectifiers turned on, and verifying a potential between the structure and a reference electrode in the ground adjacent to the test point. One known U.S. testing standard requires verification of at least 850 mV between the structure and the reference electrode.

One proposed testing methodology includes reading a polarized voltage of the pipeline by reading the pipe-to-soil voltage at test points along the pipeline (typically located 100 yards to 1 mile apart) 100 msec to 1000 msec after all cathodic protection rectifiers affecting the test point have been simultaneously turned off. Such a test is sometimes referred to herein as an "instant off" potential measurement. The polarized voltage is a measurable potential between the structure and a reference electrode in the ground adjacent to the test point. Such a test would attempt to verify at least 100mV between the pipeline structure and a reference point.

Another test, sometimes referred to as a close interval survey, involves measuring potential differences at very close intervals (around 3 feet) between the pipeline structure and adjacent soil both with cathodic protection rectifiers turned on as well as an instant after the rectifiers have been simultaneously turned off. Current close interval survey testing seeks to verify at least 100 mVolts of potential between the soil and the pipeline structure. However, conducting close interval surveys is a highly manual process, with a potential for errors, as described below. Therefore it is typical to only accomplish a close interval survey of about 20% of a pipeline in any given year.

When conducting close interval surveys, the current applied by all rectifiers affecting a particular segment of pipe are synchronously turned off and on (cycled) so that an applied voltage and a polarized voltage are recorded. Usually, survey crews are used to set up synchronized interruption equipment at each rectifier. The equipment initiates synchronized cycling and then the pipe to soil potentials are measured. Following the survey, the team returns to each rectifier location where synchronizing equipment has been temporarily installed to verify that the cycling activity occurred as expected and to remove the equipment for installation at a different pipeline segment. If the team cannot verify that the cycling activity was properly conducted at each rectifier location, the resulting collected data is rendered questionable and the survey may have to be repeated.

Underground pipelines may be adjacent to or near other structures which have ground contact and are therefore subject to corrosion. Cathodic protection systems sometimes are provided fir such structures. The structure, as well as its protection system, may interfere electrically with the cathodic protection systems for the pipeline. The interference is typically manifested as undesired currents flowing between the pipeline and the structure. To control such currents, a shunt resistance may be placed between the structure and the pipeline. Such an installation is sometimes referred to as a critical bond. Testing of critical bonds is performed to ensure that the corrosion mitigation processes in place continue to be effective, and simply to verify that the current path between the structure and the pipeline has not been opened.

There is an increasing interest in checking the polarized voltage (or instant off potential) at pipe-to-soil test points as well as the constant potential at these sites. The polarized voltage tests supply pertinent pipeline corrosion data. Further, close interval surveys are becoming more common. However, the above described testing, as currently performed, is largely manual, and difficult to synchronize, utilizing known testing equipment.

BRIEF DESCRIPTION OF THE INVENTION

In one aspect, a method for testing a cathodic protection system is provided. The system includes a cathodic protection rectifier configured to apply a voltage between a pipeline and a reference point. The method comprises measuring a magnitude of an output voltage of the cathodic protection rectifier and transmitting the measured output voltage magnitude to a site remote from the rectifier using a cellular control channel. The transmitted measurements are received at the remote site and using the transmitted measurements, it is determined whether the cathodic protection system is operational.

In another aspect, a cathodic protection rectifier system for an underground pipeline is provided. The pipeline is configured with a plurality of testing points. Each test point is an access point for making measurements and is electrically coupled to the pipeline. The system comprises at least one cathodic rectifier coupled to a power source and configured to apply a voltage across the pipeline and a ground reference point in the soil. A cathodic system monitor is coupled to the rectifier and configured to act as a switch between the rectifier and the pipeline. The cathodic system monitor is further configured to receive primary power from the power source, and to measure voltages applied to the pipeline. The cathodic system monitor also communicates the voltage measurements as pipeline test data. The system also includes a computer system configured to receive the pipeline test data from the cathodic system monitor.

In another aspect, a method for testing effectiveness of galvanic corrosion mitigation equipment along a length of an underground pipeline is provided. The equipment includes at least one cathodic protection rectifier (CPR) electrically coupled across the pipeline and a reference point through a switching device. The CPR is configured to apply a voltage to the pipeline. A plurality of test points are electrically coupled to the pipeline and dispersed at intervals along the pipeline, providing an access point for measurements. Near each test point is an reference point, which provides an electrical reference for the test point. The switching device is controlled by a cathodic system monitor which also includes a cellular modem and is configured to communicate with an external system. The method comprises applying the CPR voltages to the pipeline, measuring an output voltage of each CPR, measuring a voltage present at each test point, the voltage being measured by a test point monitor located at each test point, each test point monitor including a cellular modem and configured to transmit the voltage reading to an external system, transmitting the voltage measurements to the external system and analyzing the voltage measurements utilizing the external system.

In still another aspect, a cathodic protection system is provided. The system comprises a plurality of cathodic protection rectifiers, a plurality of switching devices, a plurality of GPS interrupters, a plurality of cathodic system monitors, and a plurality of test point monitors. The plurality of cathodic protection rectifiers are spaced at intervals along a pipeline. Each of the switching devices is configured to electrically connect one of the rectifiers to the pipeline. Each GPS interrupter is configured to control operation of at least one of the switching devices. Each of the cathodic system monitors is configured to measure an output of one of the cathodic protection rectifiers, control operation of one of the GPS interrupters, and communicate with an external system utilizing a cellular control channel. The test point monitors are spaced at intervals between the cathodic protection rectifiers, and are electrically connected across the pipeline using test points. A reference point in the ground provides a return path for electrical measurements at the test points. The test point monitors are configured to communicate with the external system utilizing a cellular control channel.

In yet another aspect, a method for performing a cathodic protection system test utilizing a plurality of test points electrically connected to a pipeline is provided. The cathodic protection system includes a plurality of test point monitors electrically coupled to various test points along the pipeline, the test points being electrically connected to the pipeline. The test point monitors are configured to communicate with an external system utilizing cellular control channel communications. A plurality of cathodic protection rectifiers are electrically coupled to the pipeline through switches, the switches being controlled by a GPS interrupter. The method comprises configuring the test point monitors to measure a voltage at the test points, concurrently opening all switches which cause a voltage from cathodic protection rectifiers to be present at a test point, measuring the test point voltages with the test point monitors, concurrently closing all switches which cause a voltage from the cathodic protection rectifier to be present at a test point, measuring the test point voltages with the test point monitors, and transmitting the measured voltages to an external system over the cellular control channel.

DETAILED DESCRIPTION OF THE INVENTION

Figure 1:
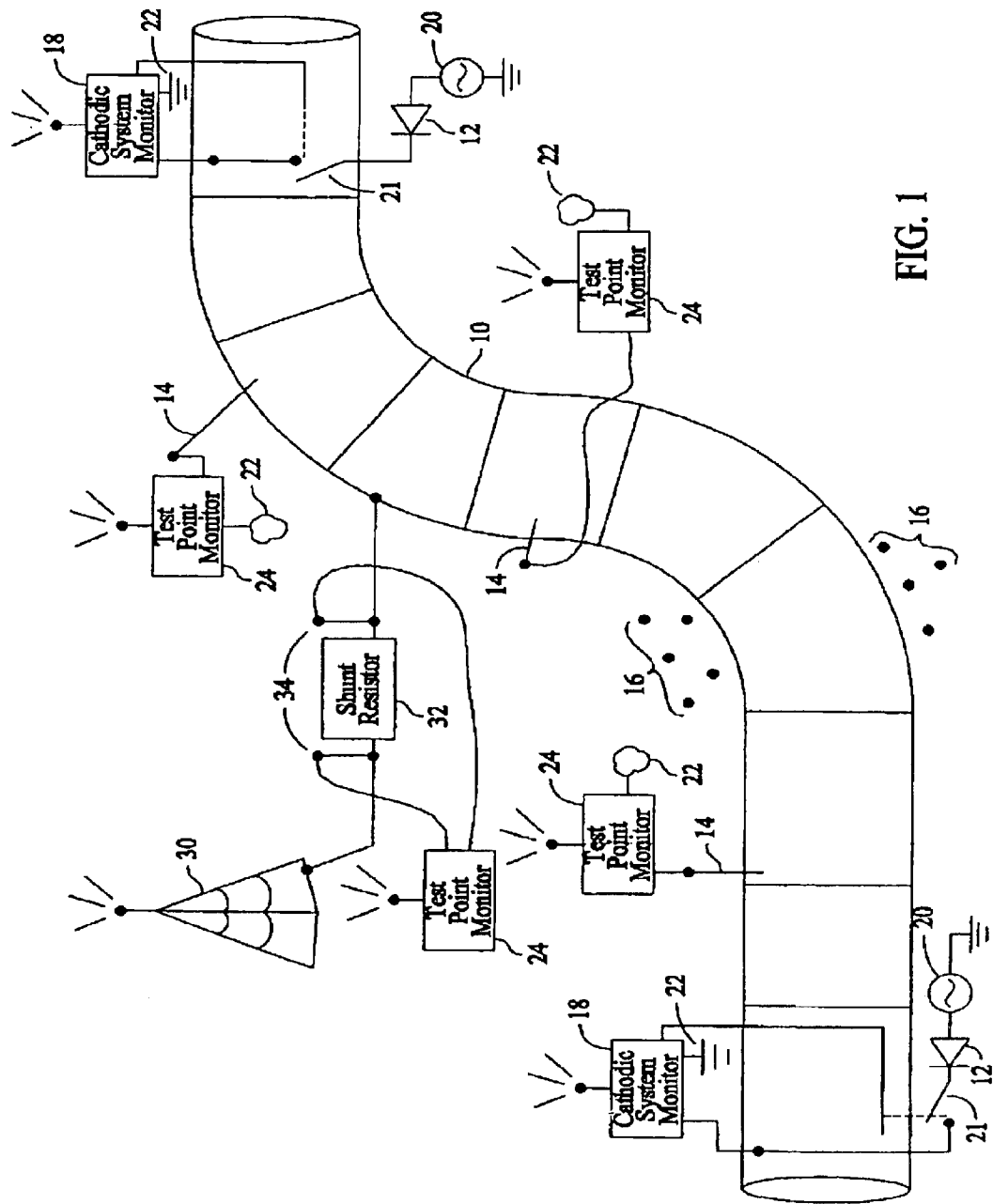
FIG. 1 is schematic illustration of a pipeline including cathodic protection systems, test points and close interval survey test points and incorporating various embodiments of pipeline remote monitoring units.

FIG. 1 is a schematic diagram of a pipeline 10 illustrating cathodic protection rectifiers 12, test points 14, and close interval survey test points 16. Cathodic system monitors 18 are utilized to measure, verify, and report output voltages and applied currents from cathodic protection rectifiers 12 on a predetermined schedule, for example, once every two months. Cathodic system monitors 18 (described further in FIG. 2) are utilized to measure applied current, in one embodiment, by measuring a voltage drop across a low resistance value resistor (e.g. a shunt resistor (shown in FIG. 2)). Monitors 18 may also be configured to monitor power 20. In a particular embodiment, monitors 18 are configured to control switching devices, for example, relays 21 which switch the voltage output from cathodic protection rectifiers 12 to pipeline 10.

Known cathodic protection rectifiers are typically placed along a pipeline, for example, every three to five miles. The rectifiers are utilized to apply a voltage across an anode bed, or reference point 22 in the soil (electrical ground) and pipeline 10. The voltage applied is approximately equal to and oppositely polarized to a voltage that naturally occurs between the pipe and soil due to galvanic corrosion and is believed to minimize a rate of corrosion. Cathodic system monitors 18 facilitate cost effective testing of cathodic protection rectifiers 12 by measuring voltages and currents output by rectifiers 12 and delivering the measurement data to an external system. Cathodic system monitors 18 are also configurable, in one embodiment, for storing and archiving the measured voltage potentials measured across pipeline 10 and a reference point in the soil, and the current applied to the pipeline through the shunt resistor. In addition, power outages in power 20 are communicated along with any other alarm events through networks as described below. An alarm event includes, but is not limited to, an out of tolerance voltage supplied by cathodic protection rectifiers 12, as measured by monitors 18.

In one embodiment, test points 14 are spaced along pipeline 10 and are utilized when reading pipe-to-soil voltages induced by cathodic protection rectifiers 12. Test points 14 are electrically connected to pipeline 10 and provide an access point for making measurements along pipeline 10. Additional voltage measurements are made shortly after rectifiers 12 have been simultaneously disconnected from pipeline 10. The voltage measurements are used to ensure continued corrosion mitigation by cathodic protection rectifiers 12. The voltage test when rectifiers 12 are simultaneously disconnected is sometimes called a polarized voltage test or an "instant off" potential measurement. Test points 14 are located at various points along a pipeline, including, but not limited to, as close as 100 yards apart to as far as one mile apart. Measurements at test points 14 are made with respect to reference points 22, sometimes called an anode bed or buried reference cell, which are in the soil and spaced along pipeline 10. Test points 14 are electrically connected to the pipeline structure, for example, through a cable, and reference points 22 are typically reference electrodes in the ground near test points 14.

Testing which utilizes test points 14 in pipelines which contain multiple cathodic protection rectifiers 12 has heretofore been unreliable, labor intensive, and has required transportation and synchronization of discrete, temporary pieces of interruption equipment at each rectifier site. Monitors 18 are configured to notify operators, as described below, if cycling is not occurring at a rectifier site. Such notification during testing eliminates a possibility that testing will have to be redone after determining that a piece of interruption equipment at a rectifier site was not working during the tests, as is the case with known testing methods.

Close interval survey test points 16 are random points in the soil all along pipeline 10 and are utilized when measuring potential (voltage) differences between the pipeline structure and adjacent soil in an effort to determine if pipeline coatings have separated and pipeline 10 has become exposed to the soil. In one close interval survey test the voltage at test points 16 are measured with all cathodic protection rectifiers 12 simultaneously connected to pipeline 10 (sometimes called a constant potential test). Another test includes synchronously switching relays 21 (cycling) to disconnect cathodic protection rectifiers 12 from pipeline 10 and measuring the voltage potentials at test points 16 in an "instant off" test, as described above. Monitors 18 are configured to notify operators if a rectifier 12 is not operating properly, ensuring reliability in the data collected in a close interval survey.

Figure 2:
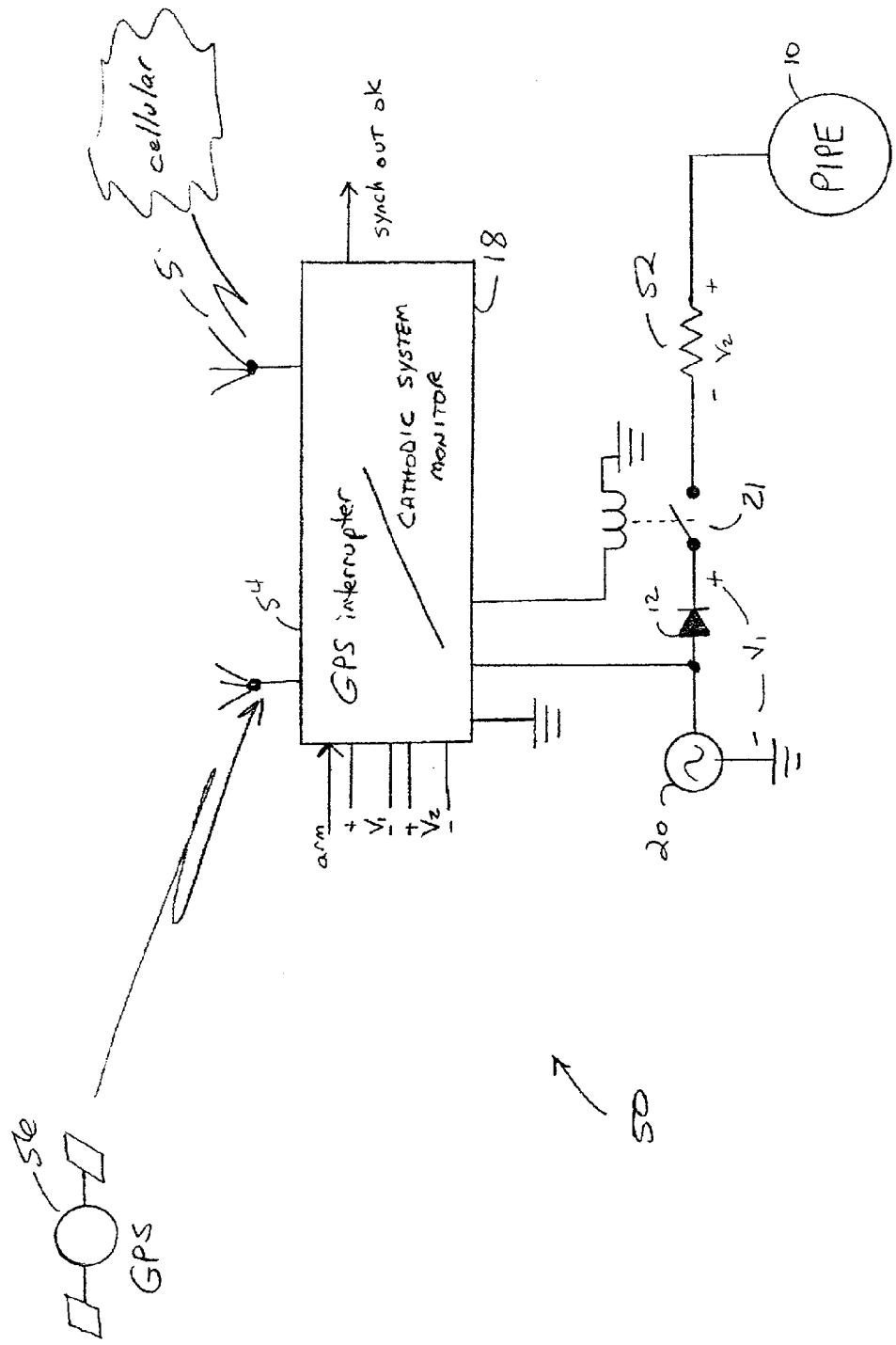
FIG. 2 is a schematic diagram of a cathodic protection system.

As described above, cathodic system monitors 18 are configured to measure and verify output voltages of rectifiers 12 and further to measure and verify current applied by rectifiers 12 using a shunt resistor (described in FIG. 2). In addition, cathodic system monitors 18, in one embodiment and as described below, are configured to emulate cellular phone communications techniques. Cathodic system monitors 18 also include provisions for accessing networks to allow a high level of monitoring and testing performance, both functionally and economically, as compared to known testing and monitoring methods. Utilization of cathodic system monitors 18 allows data affirming proper operation of cathodic protection rectifiers 12, for example, voltage potentials between the pipe and soil, to be periodically collected, stored, delivered, and archived for analysis.

In addition, power outages or out of tolerance corrosion mitigation voltages supplied by rectifiers 12 may be communicated along with other alarm events through an existing cellular network, as further described below. The cellular communications are possible as monitor 18 emulates cellular phones in order to transmit data, for example, voltages and currents, using the cellular network. The data is sent through a data gateway where it may be displayed on an Internet web site or sent secondarily to end users over email, fax, and pager links, enabling users to monitor and verify operation of monitors 18.

Pipeline 10 is further configured with, in the embodiment shown, a number of test point monitors 24, which are powered by one or more of battery and solar power. Test point monitors 24 are typically installed at test points 14 where utility power is not available. Test point monitors 24 may be configured to include most of the functionality of monitors 18 as described above. Test point monitors 24 also include the cellular communications capabilities described above. Test point monitors 24 may be configured by the user to power up at programmable intervals to perform tests including, but not limited to, collecting pipe-to-soil voltage readings, verifying proper pipe-to-soil potentials, and sensing synchronized interruption activity (switching of relays 21) on the pipeline for the purpose of taking synchronized pipe-to-soil potential readings. In addition, both monitors 18 and test point monitors 24 can perform a number of other valuable functions such as reading, storing, and archiving readings on a prescribed schedule (without transmitting readings). Further, Monitors 18 and test point monitors 24 are configured for analyzing the archived readings and transmitting statistical information about the collected values such as maximum, minimum, and average values. Monitors 18 and 24 are also able to determine whether forwarded channel information is pending in a server queue for polling or modifying operating parameters of monitors 18 and test point monitors 24 via the cellular network.

As the measurements taken by test point monitors 24 are periodic, with long periods of non-activity between testing cycles, test point monitors 24 are configured with sleep modes for conservation of battery resources. In one embodiment, described in further detail below, test point monitors 24 are configured to periodically "wake up" and determine if synchronized interruption activity is present on pipeline 10, as measured at test points 14. During this wake up cycle, test point monitor 24 measures the pipe-to-soil potential, and determines whether the source of potential (rectifiers 12) is being switched on and off (e.g. cycling) at regular intervals. The switching intervals are controlled by monitors 18 utilizing relays 21 as described above. In one specific embodiment, the switching interval is between once per second and once every 10 seconds. In this configuration, the switching interval, or cycling, of the voltage applied to pipeline 10 is implemented by cathodic system monitor 18 commanding, for example, a GPS precision interrupter (shown in FIG. 2). Pipeline 10, therefore acts as a communication media, for signaling test point monitor 24 that such readings are being requested.

Another test which can be implemented using test point monitors 24 is critical bond testing. Sometimes underground pipelines 10 are adjacent to or near other structures 30, for example radio towers or other pipelines, which have ground contact and are therefore subject to corrosion. To protect pipeline 10 and structure 30 from interfering with one another due to natural currents occurring between the two, pipeline 10 and structure 30 are electrically connected through a shunt resistance 32 placed between structure 30 and pipeline 10. Such an installation is sometimes referred to as a critical bond. Testing of critical bonds using test point monitor 24 is accomplished by measuring a voltage across shunt resistance 32 through use of shunt test points 34. Measuring the voltage across shunt resistance 32 allows operators to determine if the electrical connection between pipeline and structure 30 is intact and operating within specifications.

Physical mounting of cathodic system monitors 18 and test point monitors 24 near pipeline 10 may be accomplished using a variety of configurations. Electrically, monitors 18 are connected to both pipeline 10 (for example, at an output of rectifier 12) and to a reference point 22 in close proximity. Test point monitors 24 are connected to both pipeline 10 (for example, at a test point 14) and to a reference point 22 near the test point. Monitors 18 are typically mounted in an enclosure which includes rectifier 12. Monitors 24 may be mounted to a riser using a metal bracket. Alternatively, test point monitors 24 may be mounted at soil surface level, attached to a buried cylindrical tube also housing reference point 22. Further, test point monitors 24 may be mounted to any structure adjacent to pipeline 10 where electrical connection may be established to test points 14 and reference points 22.

FIG. 2 is a schematic diagram of a cathodic protection system 50. Power 20 is rectified for application to pipeline 10 using rectifier 12. The output of rectifier 12 is switched to pipeline 10 through a relay 21. In series between relay 21 and pipeline 10 is a shunt resistor 52. In addition to measuring the voltage output (V1) of rectifier 12, cathodic system monitor 18 is configured to measure a voltage (V2) across shunt resistor 52. Since a resistance value of shunt resistor 52 is known, measuring the voltage across shunt resistor 52 allows monitor 18 to determine a value of current applied to pipeline 10. In an alternative embodiment, a hall effect device (not shown) is used to measure applied current. As monitor 18 is configured to control relay 21, monitor 18 is able to implement synchronous switching, or cycling of the rectifier voltage, as described above.

In one embodiment, monitor 18 is configured with pre-programmed switching intervals, including, but not limited to, a start time, a stop time, an "on" period, and an "off" period. The pre-programmed switching intervals allow implementation of the synchronous testing described above. However, pipeline 10 (also shown in FIG. 1) is typically outfitted with multiple rectifiers 12 each controlled by a monitor 18. To ensure synchronicity when switching a number of rectifiers 12, monitors 18 are configured with GPS interruption circuitry 54. In an alternative embodiment, GPS interrupter 54 is physically separate from monitor 18. GPS interrupter 54 communicates with a GPS satellite 56, and therefore provides a timing mechanism which ensures that all monitors 18 (GPS interrupters 54) are programmed with an equivalent real clock time. With an equivalent real clock time, and pre-programmed switching intervals, monitors 18 are able to control synchronous application of voltages to pipeline 10 and synchronous removal of voltages from pipeline 10. In one embodiment, monitors 18 receive a "synchronization OK" signal from GPS interrupter 54, based upon received pipeline voltage and/or current measurements as compared to an applied switching interval. Through the cellular interface described below, operators can verify the pipeline testing sequence is valid (i.e. all rectifiers are being switched off and on as desired).

In one embodiment, cathodic system monitors 18 and test point monitors 24 (shown in FIG. 1) are dedicated to the task of automating collection and analysis of pipe-to-soil potentials. Monitors 18 and 24 are further configured to communicate over a cellular control channel 58 and incorporate control channel messaging as a wireless link to the end-user. In the embodiment, for example, start time, stop time, "on" period, and "off" period information is downloaded into monitors 18 over control channel 58. In such an embodiment, all communications from cathodic system monitors 18 and test point monitors 24 are in a digital format, ensuring reliable communications in areas where voice cellular coverage is marginal. In another embodiment, monitors 18 provide an arming signal to GPS interrupter 54 which initiates testing. Cellular control channel communications are desirable since only small amounts of alarm, status, and survey information need to be transported in pipeline monitoring and surveying applications. Other communications types, for example, private radio or switched telephone, cellular or landline, have been found to be cost prohibitive due to ongoing operational costs.

Figure 3:
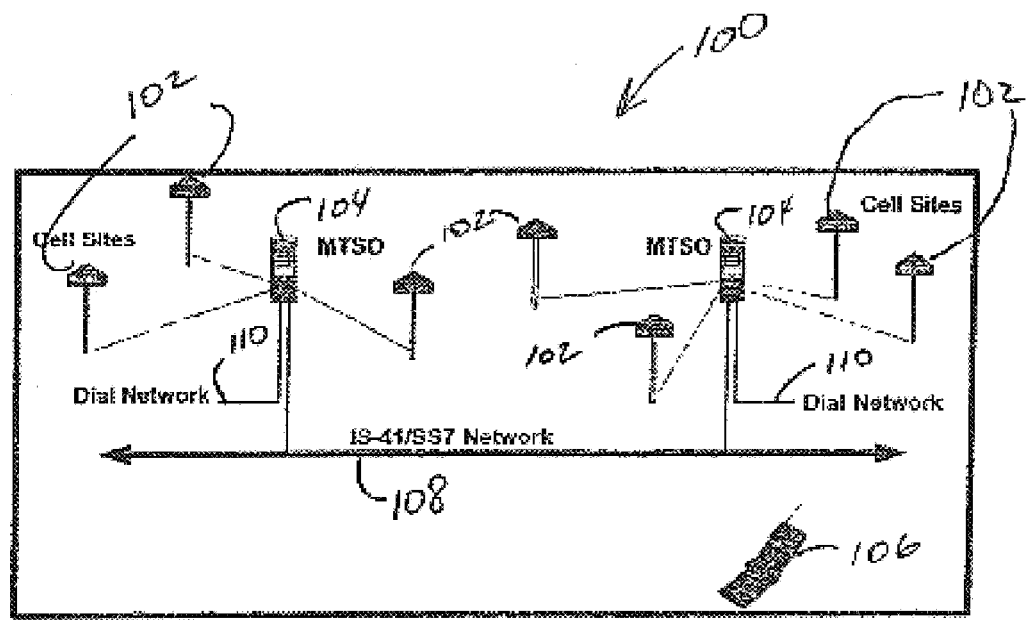
FIG. 3 is a diagram of a cellular telephone network.

Cellular control channel communications use an underutilized component of existing cellular telephone networks. A schematic diagram of such a network 100 is shown in FIG. 3. Network 100 typically includes multiple cell sites 102 or towers, a plurality of which are communicatively coupled to a mobile telephone switching office (MTSO) 104. Typical cellular networks, similar to network 100, may include multiple MTSOs 104, each communicating with multiple towers 102. Cell sites 102 transmit and receive signals to and from the individual cellular telephones 106 within a service area of the cell sites 102. The number of cell sites 102 per MTSO 104 varies according to geography and other factors. Each MTSO 104 is configured to interface to a network 108. Network 108 is, in one embodiment, an IS-41/SS7 network. Each MTSO 104 further interfaces to a local dial network 110.

Control channel communication is optimized for the transport of small packets of information over vast geographic areas at an extremely low cost. Advantages of control channel communication include that such communications utilize an existing network, utilizing proven technology, accessible in even the most remote areas. In addition, there are no capital equipment outlays necessary to establish the wide area network, no cellular telephone dialing occurs, so there are no monthly telephone line or cellular fees. Also there is no ongoing support or maintenance costs to support the wide area network.

In known cellular networks, each cellular provider uses a dedicated set, in one embodiment, about five percent, of their assigned channels as control channels. These channels are digital and are not used for voice conversations. Rather, the control channels are used solely for communicating administrative information to and from the cellular telephones in a service territory.

One known control channel communication protocol requires that each message be duplicated 5 times during each 125 msec transmission sequence, and that 3 out of 5 messages be identical for acceptance. Information delivered using the cellular control channels is also transmitted at a proportionally higher power than voice channels. During voice conversations, the cell site through which a cellular telephone is communicating is instructing the cellular telephone to reduce its power to the minimum necessary to achieve communications with that cell. The reduction in power allows reuse of the frequency at other cell sites. However, control channel power is not reduced, assuring geographical coverage even in areas where voice coverage is marginal.

Figure 4:
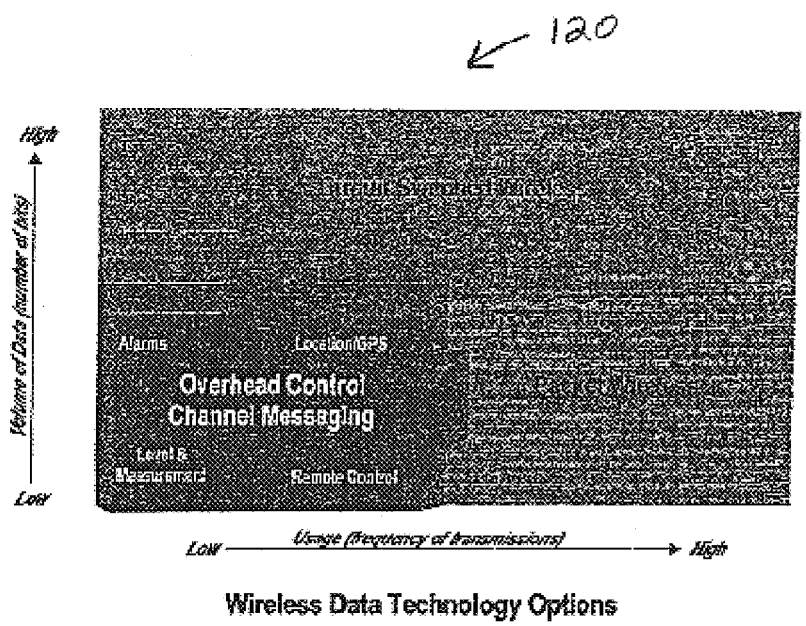
FIG. 4 is a graph comparing communication types by volume of data against frequency of cellular transmissions.

While a particular cell system may be saturated with voice calls, the control channels are still relatively available, and each one is able to process 36,000 message packets per hour. FIG. 4 is a graph 120 charting communication types by volume of data against frequency of transmissions. Chart 120 shows that control channel communications are effective for low volumes of data and relativity low update rates.

Even at the busiest times, control channels are operated at less than 25% capacity. The control channels provide many pieces of information to and from cellular telephones, using a forward channel and a reverse channel. Information is sent over forward control channels (FOCC) to instruct cellular telephones how to operate in a given service territory, identify the local system, and initiate the ringing, or paging, of cellular telephones. Reverse control channels (RECC) send dial requests and ring responses from the cellular telephones to the system along with roaming registration requests. Two functions performed by the control channels used by cellular cathodic system monitors 18 and test point monitors 24 are RECC Roaming Registration and FOCC Paging.

RECC Roaming Registration

Figure 5:
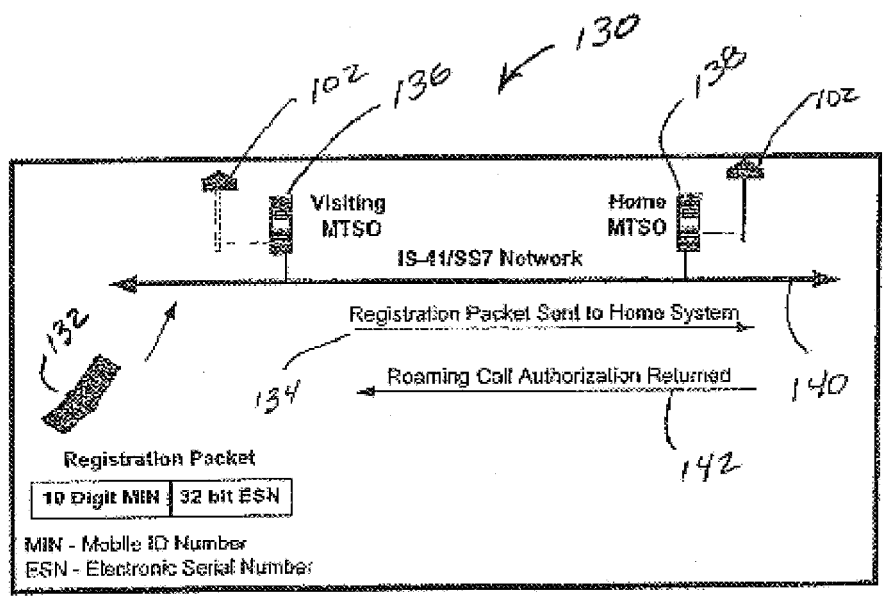
FIG. 5 is a schematic diagram of a roaming registration system for cellular telephones.

When a cellular telephone enters a non-home area, forward channel information from the nearest cell site identifies what system the phone has entered, using a System ID (SID). FIG. 5 is a diagram 130 showing roaming registration for a cellular telephone 132. Cellular telephone 132 is programmed with a home SID, and when telephone 132 recognizes that it is in a non-home area, telephone 132 automatically attempts to register itself for use in that service territory by sending a roaming registration packet 134 comprised of two pieces of information—a MIN (Mobile Identification Number) and an ESN (Electronic Serial Number) for the telephone. The MIN is the 10 digit telephone number of cellular telephone 132, and the ESN of telephone 132 is established at the time of cellular telephone manufacture.

Roaming registration packet 134 is received by the local cell at a visiting MTSO 136, which looks at the MIN to determine an SID of cellular telephone 132. MTSO 136 then instantly routes that registration packet back to the home MTSO 138, based upon received SID, over IS-41 network 140. Home mobile telephone switching office (MTSO) 138 is configured to look up account information and sends back a message 142 over IS-41 network 140 telling visiting MTSO 136 whether or not calls to be placed from cellular telephone 132 in that service territory (MTSO 136) should be allowed. Data exchange for packet 140 and message 142, takes less than ten seconds.

FOCC Paging

When a call is placed to a cellular telephone, the system sends out what is referred to as a page, the MIN or telephone number of the cellular telephone, over a Forward Control Channel (FOCC). If the call is answered by the cellular telephone, a page response is sent back and a voice channel is then assigned so that the conversation sequence may commence. Once on a voice channel the conversation never uses the control channels again. Cell and channel hand-offs are accomplished over the voice link, keeping the control channel free to process call initiation functions.

RECC Dial Feature Code Requests

The cellular network allows special features, for instance allowing users to enter instructions into the system that cause calls placed to an unanswered cellular telephone to be re-directed to another number. These dial features are entered using number sequences such as *70 314 555 1212, where the *70 is interpreted as an instruction and the number that follows (314 555 1212) as the telephone number to be dialed if the cellular telephone does not answer in a given number of ring cycles.

To establish this feature, the complete set of digits are "dialed" by sending the digit string over the cellular control channels. When received by a cellular base station, the digit string is processed by the switch and a call vectoring setup is accomplished. The RECC feature code request is one process used for data transport from a remote device, for example, cathodic system monitors 18 and test point monitors 24, across the cellular network, and back into a server for user access.

Use of Control Channels for Third-Party Messaging

By emulating the FOCC and RECC functions, third party information packets may be sent through existing cellular networks, allowing communication of data to occur virtually anywhere. As described below, a gateway is provided through which these information packets, also referred to as datagrams, are routed outside the cellular telephone network, to client-side information servers.

In one embodiment, cathodic system monitors 18 and test point monitors 24 include an embedded functional equivalent of a cellular telephone without keyboard, display, and audio circuitry. When voltage readings or alarm and status data are to be sent, a remote monitor, for example, cathodic system monitors 18 and test point monitors 24, transmit a packet of information to the closest cellular telephone tower 102 (shown in FIG. 3). This information packet looks exactly like an RECC registration packet to the existing cellular system. In the MIN field is the monitor's telephone number, one of several million numbers that are not used by wireless cellular, paging, or wireline services. In the electronic serial number (ESN) field of the registration packet are the voltage readings and alarm and status information. This information is received by the cellular network at the closest tower in the same way that a roamer registration request packet is received. However, instead of routing the packet to a distant home SID, the cellular network routes the voltage readings and alarm and status information through a gateway to at least one computer, in one embodiment a server, where it is placed into a portion of a database reserved for use and access by a particular client. The same information flow results over the cellular network regardless of whether the technology employed are RECC Dial Feature Code Requests or RECC Roaming Registration Requests.

Using the above described wireless wide area cellular network, alarm, status, and survey data from pipelines are reliably delivered from remote locations and, in one embodiment, directly into an Internet Web Page. Other client-side delivery methods are also available including automated e-mail, facsimile, pager, telnet, and Private Virtual Circuit (PVC) Frame Relay links into existing Intranet applications. In one embodiment, costs for delivery of voltage measurements, and alarm and status data are transaction-based and involve no monthly telephone line charges or cellular access fees. Therefore pipeline monitoring and surveying applications that have not been able to economically justify conventional communications techniques are brought on line and are fully accessible, for example, over the Internet.

Figure 6:
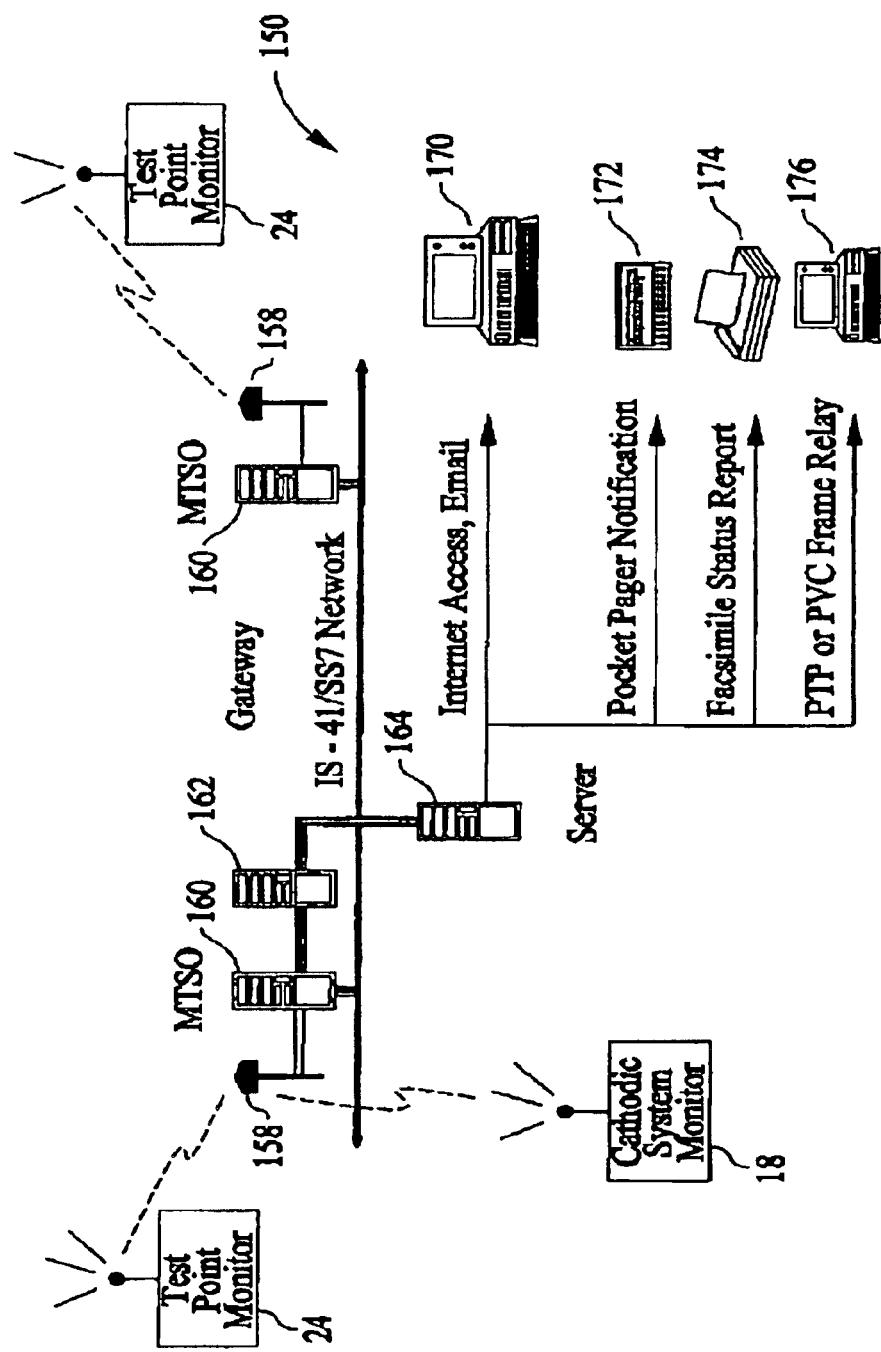
FIG. 6 is a schematic diagram of a control channel communication based pipeline monitoring system.

FIG. 6 is a diagram of a control channel communication based pipeline monitoring system 150. System 150 includes at least one of cathodic system monitors 18 and test point monitors 24 (shown in FIG. 1). Any number of cathodic system monitors 18 and test point monitors 24 arrangements are possible at pipeline 10. In one embodiment, cathodic system monitors 18 and test point monitors 24 are configured for monitoring and testing sections of pipelines, as shown in FIG. 1. In such an embodiment, cathodic system monitors 18 and test point monitors 24 are configured to periodically transmit data packets which include voltage measurements, for example, "On" potential and "instant off" potential measurements which relate to the functionality of cathodic rectifiers and pipeline protection practices, and any other pertinent information, in a digital format, to cellular tower 158. Voltage readings and other data received at tower 158 are propagated to mobile telephone switching office (MTSO) 160, where, based upon identification information contained within the data packets, the voltage readings and other data are transferred via a gateway 162 to server 164, in one embodiment, via the Internet.

Pipeline companies and companies contracted to the pipeline companies or a governmental agency, are able to access the information received from cathodic system monitors 18 and test point monitors 24 via any one of Internet access/E-mail 170, pocket pager 172 notification, facsimile 174, and PTP or private virtual circuit (PVC) frame relay 176. As shown in FIG. 6, multiple cathodic system monitors 18 and test point monitors 24, are able to transmit data packets to towers 158, thereby providing a railroad or governmental agency with an ability to data track and log the multiple test points along a pipeline using testing methodologies as described above.

Figure 7:
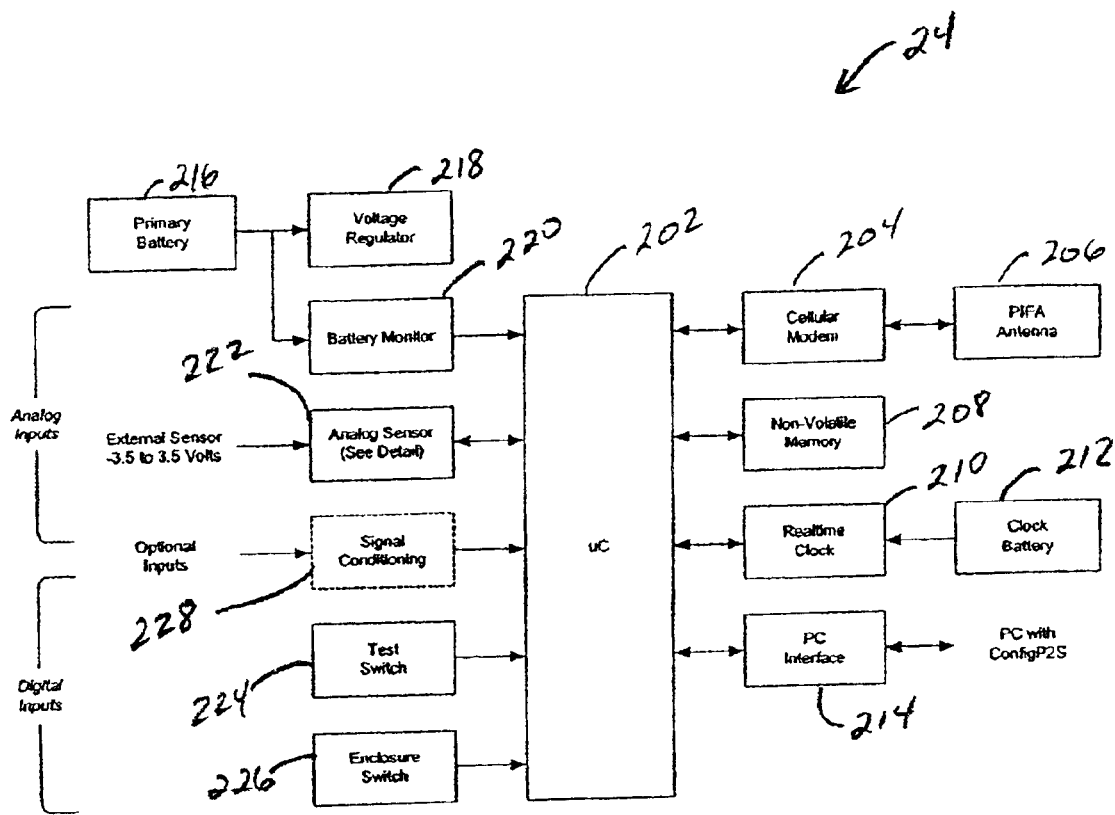
FIG. 7 is a schematic block diagram of a test point monitoring unit.

FIG. 7 is a schematic block diagram of a test point monitor 24. Test point monitor 24 includes a microcontroller 202 to which is connected a cellular modem 204 and an antenna 206, enabling the cellular control channel communications as herein described. Test point monitor 24 also includes a non-volatile memory 208, which has operating instructions for micro-controller 202 loaded therein, a real-time clock 210 and clock battery 212, and a computer interface 214 for communications with a computer to enable downloading of updated pipeline testing frequencies or testing sequences, for example.

Test point monitor 24 further includes a primary battery 216 which is connected to a voltage regulator 218 and a battery monitor 220, which is configured as an input to micro-controller 202. Other inputs to micro-controller 202 include analog sensors 222, a test switch sensor 224, an enclosure switch sensor 226, and optional signal conditioning circuits 228.

Test point monitor 24 is a low power device configured for periodic collection of pipe-to-soil voltages through the same cellular-based system used for communications with cathodic system monitors 18. To conserve power, test point monitors 24 are configured with wake-up cycles. The wake-up cycles, in one embodiment, are set at pre-programmed intervals, where test point monitor 24 powers up and checks for a cycling voltage which is being transmitted along the pipe. The cycling voltage instructs test point monitor 24 to begin performing one or more tests, typically the synchronous interruption ("instant off") tests as above described, and typically at a time during the on-off cycles that is pre-programmed into test point monitor 24. If no voltage cycling is present, or if testing is complete, test point monitor 24 powers down to a sleep mode, until the next preprogrammed power up cycle time. In another embodiment, wake-up cycles and times for measurements are transmitted directly to test point monitors 24 over the cellular control channel during a wake-up cycle.

Figure 8:
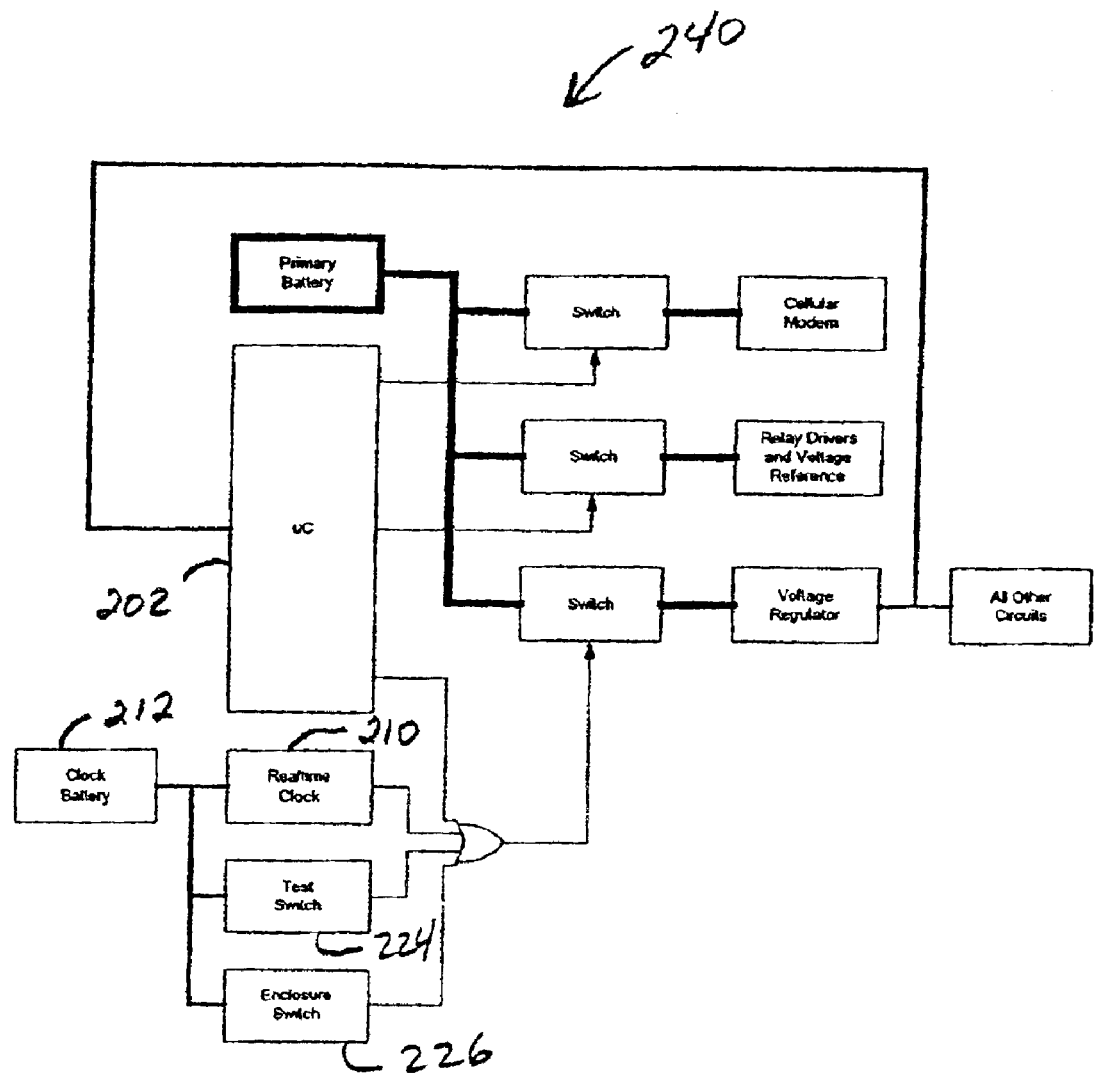
FIG. 8 is a schematic block diagram showing real-time clock functions for the test point monitoring unit shown in FIG. 7.

FIG. 8 is a schematic block diagram 240 illustrating how the above described wake-up cycles are managed within test point monitor 24. Real time clock 210, separately powered by a battery 212, is configured by microprocessor 202 to initiate a wake up at a particular date and time. Alternately, an internal tamper detection switch (enclosure switch 226) or test switch 224 may also initiate wake-up activity—in the first instance to report potential tampering with the device and in the second to execute an internal test procedure to verify correct device operation.

Once test point monitor 24 is powered-up, that is, a wake-up cycle initiated, microprocessor 202 takes control, and determines and executes the activities to be conducted during the wake-up cycle, schedules the next wake-up cycle, and causes the unit to power back down into a dormant state, with only real-time clock 210 running in preparation for the next wake-up cycle.

In addition, power outages or other alarm events along pipeline 10 are communicated through cellular network 100 (shown in FIG. 3) and secondarily to end users over email, fax, and pager links during wake-up cycles. To wake-up test point monitors 24, to begin an instant off measurement cycle, commands are delivered to monitors 18, as described above over the cellular network or other means, which are deployed over wide geographic territories, instructing monitors 18 to begin a preprogrammed synchronous interruption cycling, using GPS-derived timing, transmitted to and from GPS interrupter 54. By obtaining synchronization using commonly available GPS as a time base, asynchronous activation of devices over a relatively slow and non-synchronized cellular communication link ultimately establishes a very tightly controlled process. The process includes simultaneous rectifier on-off cycling of cathodic protection rectifiers 12, which is necessary for timing synchronized instant off readings from test points 14, thereby eliminating an error prone manual process. Further, a synchronization system incorporating cathodic system monitors 18 is activated, and in one embodiment, can verify that high current levels are, in fact, being properly controlled, through a feedback process, allowing the user to verify proper coordinated cycling before the time and expense of actual close interval data collection.

Test point monitors 24 are configurable for a variety of functions, including, but not limited to, log voltages then sleep, send voltages then sleep, check for communications, reading voltages, do not send voltages until an alarm is turned on, analyze stored readings, send statistical information, check for oscillations and turn on/off cathodic protection systems.

Figure 9:
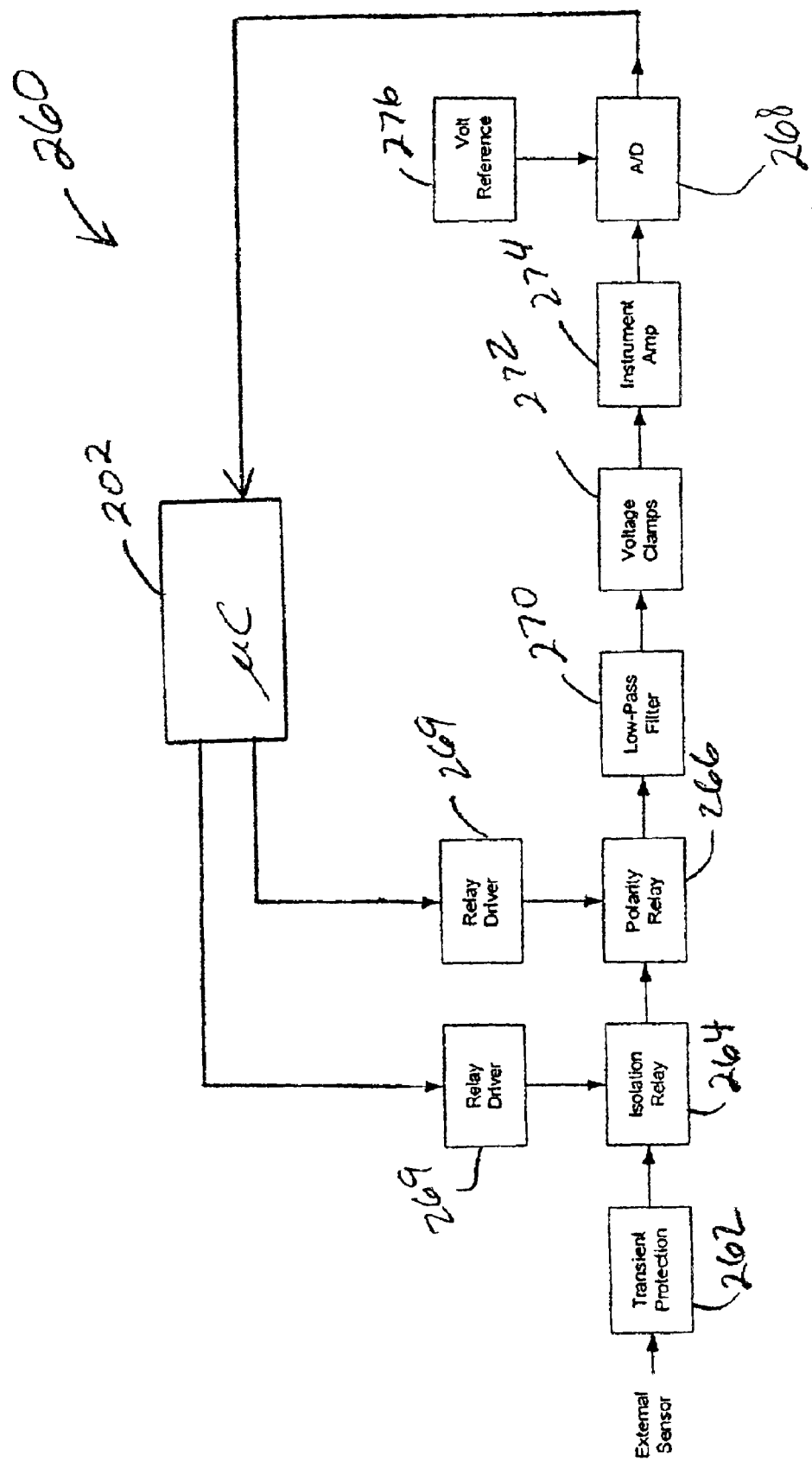
FIG. 9 is a functional block diagram for the test point monitoring unit shown in FIG. 7.

FIG. 9 is a schematic block diagram of an analog input monitoring channel 260 illustrating circuitry through which test point monitors 24 perform pipe-to-soil voltage testing. It is important to collect accurate readings from test points, and to filter out other induced voltages that may manifest as voltage offset errors. Analog input monitoring channel 260 is configured with a high input impedance to prevent affecting the polarization of the test point and measurement of the very low signal level. The voltage reading is taken between the pipeline test points 14 (shown in FIG. 1) itself and buried reference cells 22 (shown in FIG. 1) which are in close proximity to pipeline 10 (shown in FIG. 1). Typically, reference cells 22 enhance conductivity with the soil and impose a DC voltage offset that is factored out of the reading taken by at the test points. Analog input monitoring channel 260 also provides transient protection 262.

Test point monitors 24 contain an isolation relay 264 that provides isolation from test points 14. Isolation relay 264 delivers an infinite input impedance except for those very brief time periods, in one embodiment less than 1 second, when readings are actually being taken, as instructed by microcontroller 202 (also shown in FIG. 8). Following isolation relay 264 is a polarity relay 266 used by microcontroller 202 to establish positive or negative polarity—allowing a single ended analog to digital converter 268 to be used in a bipolar environment. Microcontroller 202 is configured to control opening and closing of relays 264 and 266 through use of relay drivers 269.

A low pass filter 270 eliminates rectified RF noise from high frequency sources and high noise sources, for example, nearby light rail trains and a voltage clamp 272 and an instrumentation amp 274 further cleans the signal from the test point, for measurement by A/D converter 268, which compares the signal to a reference 276. Finally, under direction of microprocessor 202, and in one specific embodiment, between 512 and 1024 readings are taken and averaged at a multiple of 16.67 millisecond and 2.50 millisecond intervals to eliminate the effect of inductively coupled noise signals, for example, from 60 Hz overhead power lines and 400 Hz power transmission sources.

By using the synchronized interruption process, cathodic system monitors 18 and test point monitors 24 are able to read, average, and deliver "instant off" potential readings, without the manual placement of synchronization instruments, as in the known manual process. In such a configuration, rectifier current cycling of cathodic protection rectifiers 12 under control of monitors 18, and the pipeline itself act as a command and communication media for signaling test point monitors 24 that such a reading is being requested.

Using available overhead control channels of the cellular telephone network, a battery-powered or solar powered test point monitor, for example, test point monitor 24, can read and transport pipe-to-soil voltage readings, and other pipeline test data, that are presently collected on a manual basis involving travel to each remote site. In addition, test point monitors 24 can determine when alarm conditions have developed, such as out of tolerance of pipe-to-soil potentials, and alert users to these conditions. Also, and as described above, test point monitors 24 can detect when synchronized interruption is occurring, take a particular reading during the interruption, and forward this reading to a centralized location. By providing the cellular communications whereby this information can be delivered into a centralized database, users can retrieve pipe-to-soil potential data over the Internet, or it may be forwarded through techniques such as email, facsimile, pocket pager or other data networking connections.

Figure 10:
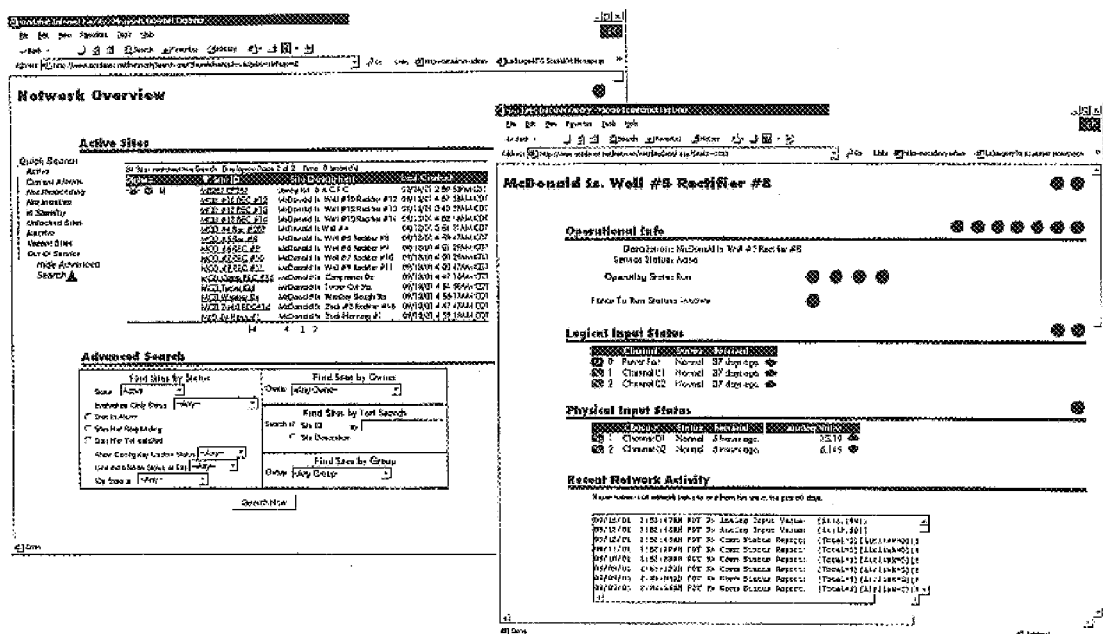
FIG. 10 is one embodiment of a pipeline monitoring data web page.

FIG. 10 is one embodiment of a web page 300 where a user can access pipeline test data. Regardless of which the above described wireless technologies are used, the network servers provide routing nodes for information passing to and from monitors 18 and test point monitors 24. Networks typically utilize the Internet as a means of user access, not only for communication with monitors 18 and test point monitors 24, but for establishing and administrating users, configuring network behavior, and managing real-time and historical data. Page 300 is but one example of web pages that are used to gather data from, and change operating and testing parameters for one or more of cathodic system monitors 18 and test point monitors 24. Specific functionalities are accessible from web pages similar to web page 300 are as follows:

Alarms and Status Data

Authorized end users can view data from many monitors 18 and test point monitors 24 at once using a network view web page or they can go to detailed status screens showing the condition of every monitored channel at individual pipeline testing sites. Along with channel conditions, important data such as communication metrics and historical alarm and notification data are available. Through data entry screens available to system administrators, channel names, alarm nomenclature, engineering units, and other site-specific data is entered into the network.

E-mail Alarm Notification

Alarms and automatic voltage readings can cause automatic email notifications to be triggered to any number of recipients. E-mail addressees may be ranked by priority and different timing criteria may be established allowing secondary notification to alternate groups if any alarm condition persists beyond a desired limit. E-mails contain a URL (an Internet link) that when selected with a mouse click, brings up a web page specific to any one of monitors 18 and test point monitors 24. The user can then examine the detailed view of the monitor for channel condition verification or for activation of output functions. In addition to e-mail notification, alarms may be routed to recipients using alphanumeric pagers and facsimile devices. In all cases, the channel names and other nomenclature programmed into the data base through the Internet by the system administrator becomes the "vocabulary" used by the server to compose messages for the various notification and display schemes.

Administrative Functions

A comprehensive set of administrative functions and procedures provide users with complete control over all aspects of the pipeline monitoring system operation. Designated system administrators can control the level of access by their users. Individual users can configure the type and detail of information viewable at various levels of view depth. Built-in procedures also monitor all aspects of pipeline monitoring system performance on a real-time basis. Any system anomalies, security breaches, or perceived degradation of communication functions are immediately made available to system administrators via the same notification schemes used for actual alarms and status reporting—over e-mail, fax, and pocket pager. The system also provides information when any of monitors 18 and test point monitors 24 have not reported in with a health check message at the appointed time, providing another level of system integrity confirmation.

Report Generation

A full suite of automated reports is available through web pages allowing the user to analyze network and unit performance and to summarize alarm data on a periodic basis. All polling and control activity is identified by precise time and date stamps, along with an indication of which user performed the activity. Monitors 18 and test point monitors 24 are programmable to take readings and forward summaries to recipients, allowing daily reporting tasks to be automated. User-selectable report templates allow users to organize data in a variety of ways facilitating the task of collecting voltage and current data from cathodic protection rectifiers to assure proper corrosion protection system performance.

Figure 11:
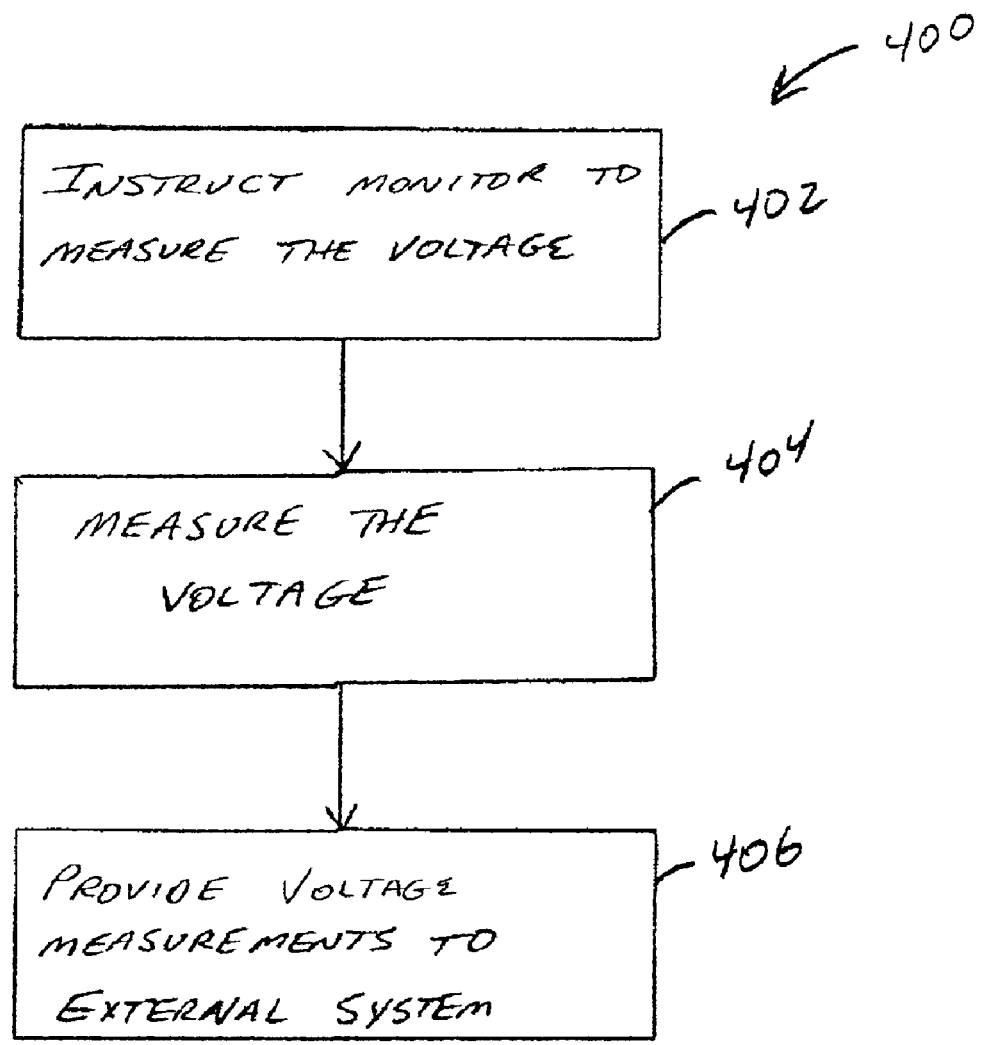
FIG. 11 is a flowchart illustrating a method implemented by test point monitors.

FIG. 11 is a flowchart of a voltage measurement method 400 implemented by monitors 18 and test point monitors 24 (shown in FIG. 1). The method is similar in that both monitors 18 and test point monitors 24 are measuring voltages, although monitor 18 is typically measuring an output of a cathodic protection rectifier 12 and test point monitor 24 measures a voltage present at a test point 14 along a pipeline. First, a monitor is instructed 402 to measure voltages. The monitor measures 404 the voltages, and provides 406 the voltage measurements to an external system as herein described.

Figure 12:
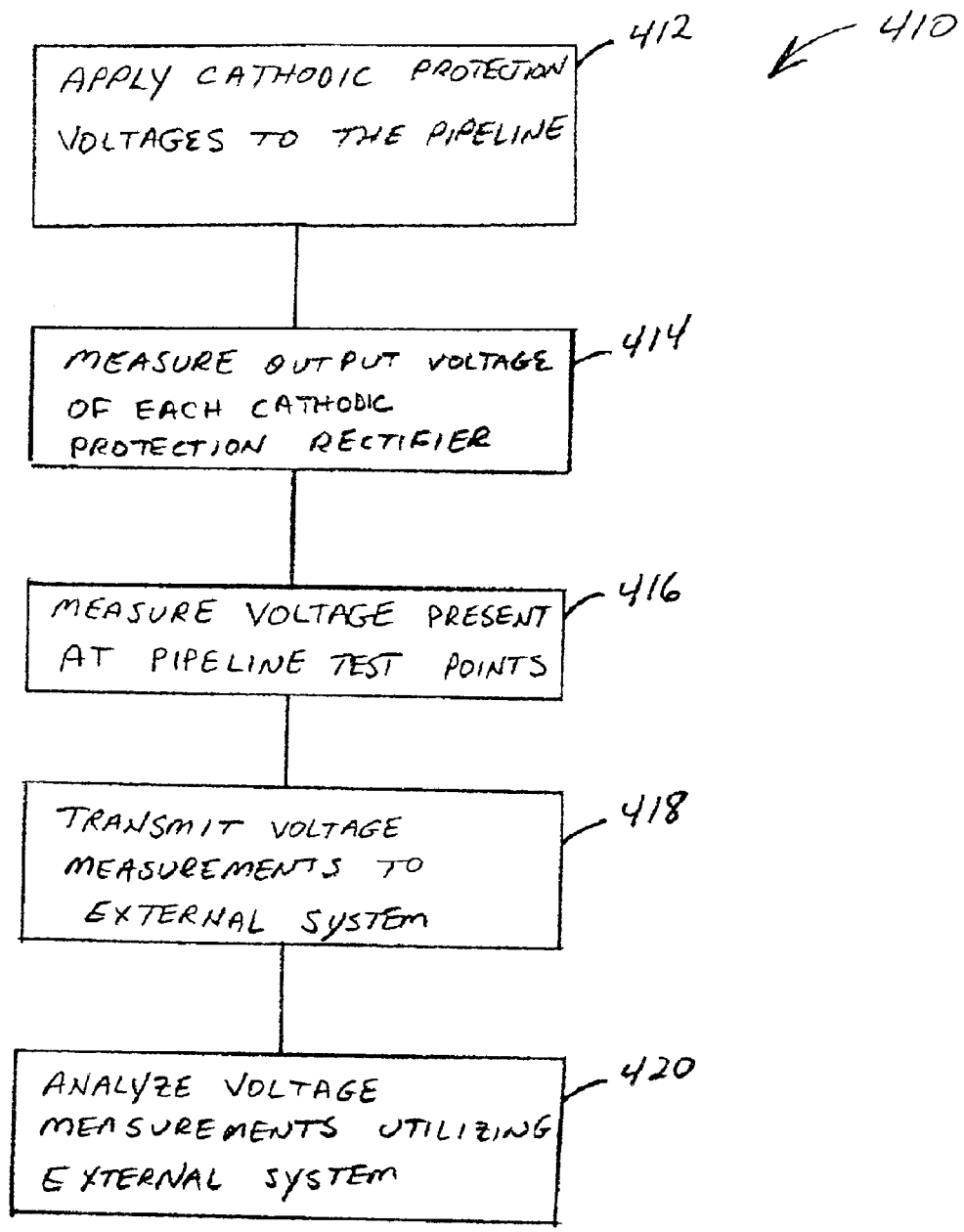
FIG. 12 is a flowchart illustrating a method for testing effectiveness of galvanic corrosion mitigation equipment installed along underground pipelines.

FIG. 12 is a flowchart of a method 410 for testing effectiveness of galvanic corrosion mitigation equipment, as described above, installed along underground pipeline. The method is incorporated utilizing cathodic system monitors 18 and test point monitors 24, (shown in FIG. 1) where cathodic system monitors 18 are configured with a switching device to control application and removal of a voltage to the pipeline, supplied by cathodic protection rectifier 12. First, cathodic protection rectifier voltages are applied 412 to the pipeline and an output voltage of each cathodic protection rectifier is measured 414. Each test point 14 (shown in FIG. 1) is measured 416 for a voltage, the voltage being measured by test point monitors 24 located at each test point 14. The voltage measurements are transmitted 418 to the external system and are analyzed 420 utilizing the external system.

Figure 13:
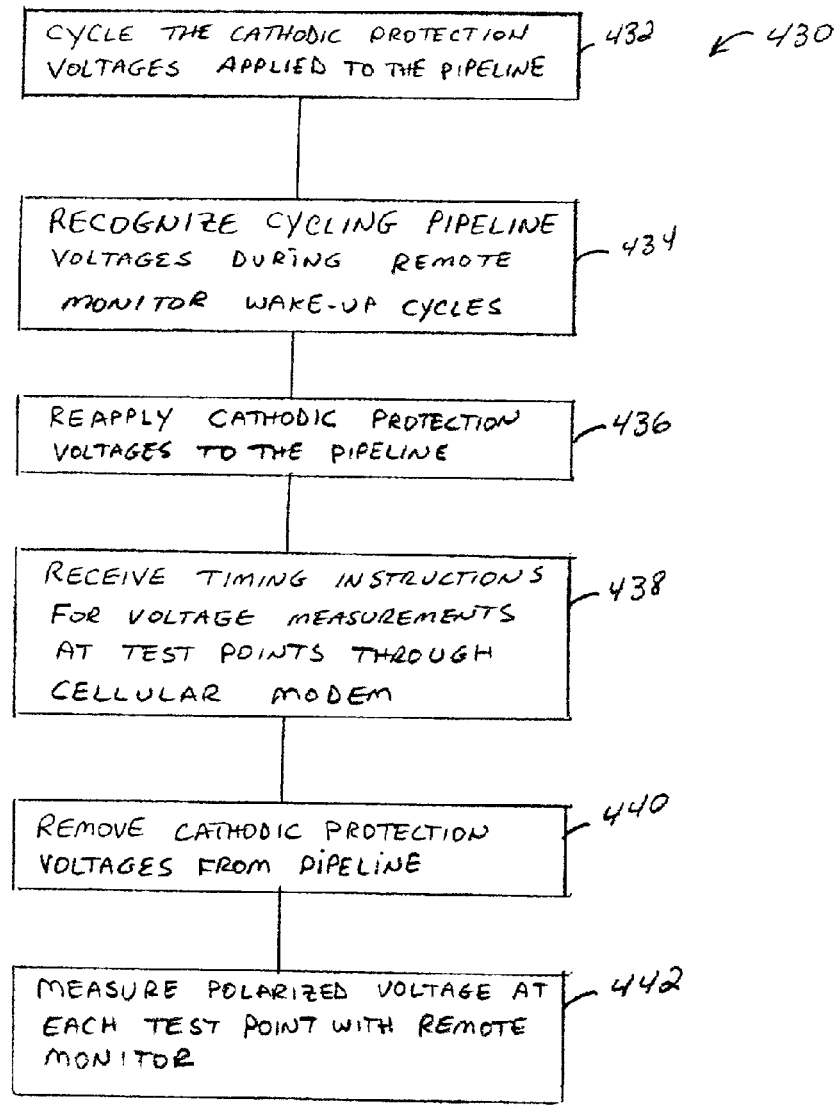
FIG. 13 is a flowchart illustrating a method of obtaining polarized voltage measurements along the pipeline.

FIG. 13 is a flowchart illustrating a method 430 of obtaining a polarized voltage of the pipeline. It is to be recognized that the illustrated method 430 can be incorporated with method 410 illustrated in FIG. 12. To implement method 430 test point monitors 24 at test points 14 are configured with a wake-up mode controlled by a real time clock. First, the cathodic protection rectifier voltages on the pipeline are cycled 432. The voltage cycling is then recognized 434 at each test point 14 during wake-up cycle of each test point monitor 24. The cathodic protection rectifier voltages are re-applied 436 to the pipeline. Concurrently, each test point monitor 24 receives 438 a time to make a voltage measurement at the respective test point 14 through its cellular modem. Shortly before that time, the cathodic protection rectifier voltages are removed 440 from the pipeline and a polarized voltage is measured 442 at each test point 14.

Use of cathodic system monitors 18 and test point monitors 24, as described above, provides an economical solution to the described problems of synchronization of cathodic protection rectifiers 12, when performing "instant off" or polarized portions of close interval surveys by incorporating the Internet and cellular telephone networks 100. Further pipe-to-soil voltage tests at test points 14 are accomplished without having survey teams physically present at the test points 14. The combination of test point monitors 24 and the pipe further provide a means of delivering alarms from pipe-to-soil testing to end users, including instant off testing.

Such testing methodologies provide for a cost effective and accurate testing, which is important to pipeline companies which operate pipelines, that can stretch many miles in length and incorporate dozens of cathodic protection rectifiers 12 and test points 14, thereby replacing days of manual surveying done by testing teams, and therefore allowing for more frequent pipe-to-soil testing, including testing which incorporates synchronized turning off and on of cathodic protection rectifiers 12.

While the invention has been described in terms of various specific embodiments, those skilled in the art will recognize that the invention can be practiced with modification within the spirit and scope of the claims.

What is claimed is:

1. A method for testing a cathodic protection system, the system including at least one cathodic protection rectifier configured to apply a voltage across a pipeline and a reference point, said method comprising:

measuring a magnitude of an output voltage of the cathodic protection rectifer;

transmitting, to a site remote from the rectifier, the measured output voltage magnitude using a cellular control channel;

receiving, at the remote site, the transmitted measurement; and determining, using the transmitted measurement, whether the cathodic protection system is operational.

2. A method according to claim 1 further comprising:

inserting a shunt resistor in series between an output of the cathodic protection rectifier and the pipeline;

measuring a voltage drop across the shunt resistor, calculating an amount of current applied to the pipeline using the measured voltage drop; and transmitting the calculated current amount to the remote site.

3. A method according to claim 2 further comprising archiving at least one of the voltage measurements and calculated currents within a memory of a cathodic system monitor.

4. A method according to claim 3 further comprising:

deriving statistical information on the archived voltage measurements and calculated currents; and transmitting the statistical information to the remote site.

5. A method according to claim 1 further comprising:

measuring a voltage potential at one or more test points located a distance from the cathodic protection rectifier using a test point monitor; and transmitting the measured test point voltages to the remote site, from the test point monitor, using the cellular control channel.

6. A method according to claim 5 wherein the test points are located at least 100 yards from the cathodic protection rectifier.

7. A method according to claim 5 further comprising archiving the voltage potentials measured at the test points within a memory of the test point monitor.

8. A method according to claim 7 further comprising:

deriving statistical information on the archived voltage potential measurements; and transmitting the statistical information to the remote site, from the test point monitor, using the cellular control channel.

9. A method according to claim 5 wherein measuring a voltage potential at one or more test points comprises measuring the voltage during at least one of when all cathodic protection rectifiers are turned on and when all cathodic protection rectifiers are turned off.

10. A method according to claim 9 wherein measuring the voltage when all cathodic protection rectifiers are turned off comprises measuring the voltage within one second after turning all cathodic protection rectifiers off.

11. A method according to claim 1 further comprising:
using a hall effect device coupled to a cathodic system monitor to measure a current output of the cathodic protection rectifier; and
transmitting the calculated current amount to the remote site, from the cathodic system monitor, using the cellular control channel.

12. A cathodic protection rectifier system for an underground pipeline, the pipeline configured with a plurality of test points along a length of the pipeline, each electrically connected to the pipeline, said system comprising:
at least one cathodic rectifier coupled to a power source and configured to apply a voltage across the pipeline and a reference point in the soil;
a cathodic system monitor coupled to said rectifier, said monitor configured to control a switch located between said rectifier and the pipeline, said monitor further configured to measure voltages applied to the pipeline and to communicate the voltage measurements as pipeline test data, said cathodic system monitor configured to communicate utilizing a control channel of a cellular network; and
a computer system configured to receive the pipeline test data from said cathodic system monitor.

13. A cathodic protection rectifier system according to claim 12 further comprising at least one test point monitor, each said test point monitor configured to communicate on a control channel of a cellular network each said test point monitor electrically connected between one of the testing points and a corresponding reference point in the soil, configured to measure a voltage present at a test point, with respect to the corresponding reference point, a voltage having been applied to said pipeline by said cathodic rectifier, and configured to communicate the test point voltage measurement as pipeline test data to said computer system.

14. A cathodic protection rectifier system according to claim 13, said system further comprising a cellular system configured to receive communications on the cellular control channel from said cathodic system monitor and said test point monitors, said cellular system comprising:
at least one cellular tower;
a mobile telephone switching office (MTSO) connected to said towers; and
a gateway connected to said MTSO and connected to said computer system.

15. A cathodic protection rectifier system according to claim 14 wherein said computer system comprises a server configured to retrieve pipeline test data from said cellular system.

16. A cathodic protection rectifier system according to claim 15 wherein said server is an internet server.

17. A cathodic protection rectifier system according to claim 15 wherein said server is configured to provide at least one of internet access, E-mail notification, pocket pager notification, facsimile reports, and Private Virtual Circuit (PVC) Frame Relay links.

18. A cathodic protection rectifier system according to claim 15 wherein said server is configured with at least one web page for display of pipeline test data.

19. A cathodic protection rectifier system according to claim 15 wherein pipeline test data includes voltage measurements, channel conditions, communication metrics, historical alarm and notification data.

20. A cathodic protection rectifier system according to claim 15 wherein pipeline test data is identified by date and time stamps and an indication of which user performed the activity resulting in the pipeline test data.

21. A method for testing effectiveness of galvanic corrosion mitigation equipment along a length of an underground pipeline, the equipment including at least one cathodic protection rectifier (CPR) electrically coupled to the pipeline and a reference point, the pipeline coupling through a switching device, the CPR configured to apply a voltage to the pipeline, and a plurality of test points electrically connected to the pipeline and dispersed at intervals along the pipeline, the switching device being controlled by a cathodic system monitor which also includes a cellular modem and is configured to communicate with an external system utilizing cellular control channel communications, said method comprising:
applying the CPR voltages to the pipeline;
measuring an output voltage of each CPR;
measuring a voltage present at each test point, the voltage being measured by a test point monitor located at each test point, each test point monitor including a cellular modem and configured to transmit the voltage reading to an external system;
transmitting the voltage measurements to the external system over the cellular control channel; and
analyzing the voltage measurements utilizing the external system.

22. A method according to claim 21 wherein the test point monitors at the test points are configured with a wake-up mode controlled by a real time clock within the test point monitors, said method further comprising:
cycling the CPR voltages on the pipeline;
recognizing the voltage cycling at each test point during a wake-up cycle of each test point monitor;
removing the CPR voltages from the pipeline; and
measuring a voltage at each test point.

23. A method according to claim 22 wherein cycling the CPR voltages further comprises:
transmitting a command to begin voltage cycling from the external system to the cellular modems of the cathodic system monitors controlling the switching devices; and
executing commands within the cathodic system monitors to cycle the switching device.

24. A method according to claim 22 wherein removing the CPR voltages from the pipeline comprises executing a command to open the switching device.

25. A method according to claim 24 wherein the command to open the switching device is received utilizing at least one of receiving a command through the cellular modem of the cathodic system monitor, executing a preloaded algorithm, and operation of a manual switch.

26. A method according to claim 22 wherein the measurement of a voltage at each test point is within one second of removing the CPR voltages from the pipeline.

27. A method according to claim 22 wherein all CPR voltages applied to the pipeline are removed simultaneously.

28. A cathodic protection system, comprising:
a plurality of cathodic protection rectifiers spaced at intervals along a pipeline;
a plurality of switching devices, each said switching device configured to electrically connect one of said rectifiers to the pipeline;
a plurality of GPS interrupters, each interrupter configured to control operation of at least one of said switching devices;
a plurality of cathodic system monitors, each of said cathodic system monitors configured to measure an output of one of said cathodic protection rectifiers, and further configured to control operation of one of said GPS interrupters, said cathodic system monitors configured to communicate with an external system utilizing a cellular control channel; and a plurality of test point monitors spaced at intervals between said cathodic protection rectifiers, and electrically connected between the pipeline and a reference point, the reference point being a ground reference for said test point monitors, said test point monitors configured to communicate with the external system utilizing a cellular control channel.

29. A cathodic protection system according to claim 28 wherein said cathodic system monitors are configured to measure an output voltage of said cathodic protection rectifiers.

30. A cathodic protection system according to claim 28 further comprising a shunt resistance between each said switch and the pipeline, said cathodic system monitors configured to:

measure a voltage across said shunt resistance; and determine a current output of said cathodic protection rectifier based upon the voltage measured.

31. A cathodic protection system according to claim 28 further comprising a hall effect device electrically coupled to each said cathodic system monitor, said cathodic system monitors configured to determine a current output of said cathodic protection rectifiers based upon an output of said hall effect device.

32. A cathodic protection system according to claim 28 wherein said GPS interrupters are configured to conduct testing of said cathodic protection rectifiers, said GPS interrupter being configured to control operation of said switching devices utilizing at least one of a start time, a stop time, an on period, and an off period.

33. A cathodic protection system according to claim 32 wherein said GPS interrupters are configured to synchronize the testing of said cathodic protection rectifiers utilizing a time received from a GPS satellite.

34. A cathodic protection system according to claim 33 wherein said cathodic system monitor is configured to provide an arming signal to a corresponding said GPS interrupter, the arming signal enabling said GPS interrupters to perform synchronized testing of said cathodic protection rectifiers.

35. A cathodic protection system according to claim 33 wherein said cathodic system monitor is configured to provide the arming signal based upon a communication received over a cellular control channel.

36. A cathodic protection system according to claim 33 wherein said GPS interrupter is configured to provide a synchronization OK signal to a corresponding said cathodic system monitor, the synchronization OK signal signifying that said GPS interrupter has determined that an output signal of said cathodic protection rectifier is synchronous with a signal used for controlling operation of said switching device.

37. A cathodic protection system according to claim 36 wherein said cathodic system monitor is configured to notify the external system utilizing the cellular control channel if the synchronization OK signal is not received from said GPS interrupter.

38. A cathodic protection system according to claim 28 wherein said test point monitors are configured to measure voltages present between the pipeline and the reference point, and transmit the voltages measured to the external system over the cellular control channel.

39. A cathodic protection system according to claim 28 wherein said GPS interrupters are configured to periodically switch all switching devices thereby inducing voltage on and voltage off cycles on the pipeline, said test point monitors configured with wake-up cycles, during a wake up cycle said test point monitors configured to:

recognize the voltage off and on cycles induced onto the pipeline measure the voltages present on the pipeline at pre-programmed intervals stored in the test point monitors, and based upon the voltage cycles;

store the voltage measurement within a memory of said test point monitor; and transmit the measured and stored voltages over a cellular control channel to an external system.

40. A cathodic protection system according to claim 28 wherein said cathodic system monitors and said test point monitors are configured to measure a voltage present on the pipeline within one second after said GPS interrupters open all of said switching devices.

41. A cathodic protection system according to claim 28 wherein said cathodic system monitors and said test point monitors are configured to measure a voltage present on the pipeline after said GPS interrupters close all of said switching devices.

42. A cathodic protection system according to claim 28 further comprising at least one critical bond between the pipeline and a nearby structure, the nearby structure being subject to galvanic corrosion, said critical bond comprising a shunt resistance between the pipeline and the structure, said system configured to periodically monitor a voltage across the shunt resistance utilizing one of said test point monitors, said test point monitors configured with wake-up cycles, the periodic monitoring of the voltage occurring during the wake up cycle.

43. A method for performing a cathodic protection system test utilizing a plurality of test points electrically connected to a pipeline, the cathodic protection system including a plurality of test point monitors electrically coupled to one or more of the test points along the pipeline and configured to communicate with an external system utilizing a cellular control channel, and a plurality of cathodic protection rectifiers coupled to the pipeline through switches, the switches being controlled by a GPS interrupter, said method comprising:

configuring the test point monitors to measure a voltage at the test points;

concurrently opening all switches which cause a voltage from the cathodic protection rectifier to be present at a test point;

measuring the test point voltages with the test point monitors;

concurrently closing all switches which cause a voltage from the cathodic protection rectifier to be present at a test point;

measuring the test point voltages with the test point monitors; and transmitting the measured voltages to an external system over the cellular control channel.

44. A method according to claim 43 wherein:

configuring the test point monitors comprises configuring the test point monitors with a wake up cycle;

concurrently opening all switches comprises concurrently opening all switches during the wake up cycle; and concurrently closing all switches comprises concurrently closing all switches during the wake up cycle.

* * * * *